(12) United States Patent
Hiestand et al.

(10) Patent No.: US 9,187,405 B2
(45) Date of Patent: Nov. 17, 2015

(54) S1P RECEPTOR MODULATORS FOR TREATING RELASPING-REMITTING MULTIPLE SCLEROSIS

(71) Applicants: Peter C. Hiestand, Austria (CH); Christian Schnell, Hesingue (FR)

(72) Inventors: Peter C. Hiestand, Austria (CH); Christian Schnell, Hesingue (FR)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/257,342

(22) Filed: Apr. 21, 2014

(65) Prior Publication Data

US 2014/0228446 A1 Aug. 14, 2014

Related U.S. Application Data

(60) Division of application No. 13/149,468, filed on May 31, 2011, now Pat. No. 8,741,963, which is a continuation of application No. 12/303,765, filed as application No. PCT/EP2007/005597 on Jun. 25, 2007, now abandoned.

(30) Foreign Application Priority Data

Jun. 27, 2006 (GB) .................................. 0612721.1

(51) Int. Cl.
*A61K 31/13* (2006.01)
*C07C 215/08* (2006.01)
*A61K 31/137* (2006.01)
*A61K 31/397* (2006.01)

(52) U.S. Cl.
CPC ............. *C07C 215/08* (2013.01); *A61K 31/137* (2013.01); *A61K 31/397* (2013.01); *A61K 31/13* (2013.01)

(58) Field of Classification Search
CPC .............................. A61K 31/13; A61K 31/137
USPC ................................................. 514/667, 903
See application file for complete search history.

(56) References Cited

U.S. PATENT DOCUMENTS

2006/0046979 A1 3/2006 Hiestand
2014/0228446 A1 8/2014 Hiestand et al.

FOREIGN PATENT DOCUMENTS

| RU | 2199339 C2 | 2/2003 |
| RU | 2278687 C1 | 6/2006 |
| WO | 03/097028 | 11/2003 |
| WO | 03/099192 | 12/2003 |
| WO | 2004/028521 | 4/2004 |
| WO | 2004/050073 | 6/2004 |
| WO | 2004/113330 | 12/2004 |
| WO | 2005123104 A2 | 12/2005 |
| WO | 2006/055809 | 5/2006 |
| WO | 2006/058316 | 6/2006 |
| WO | 2006/066086 | 6/2006 |

OTHER PUBLICATIONS

Xie et al., "Sphingosine-1-Phosphate Receptor Agonism Impairs the Efficiency of the Local Immune Response by Altering Trafficking of Naive and Antigen-Activated CD + T Cells", J Immunol; vol. 170, pp. 3662-3670, 2003.
Budde et al., "First Human Trial of FTY720, a Novel Immunomodulator, in Stable Renal Transplant Patients". J Am Nephrol, vol. 13, pp. 1073-1083, 2002.
Kataoka et al., "FTY720, Sphingosine 1-Phosphate Receptor Modulator, Ameliorates Experimental Autoimmune Encephalomyelitis by Inhibition of T Cell Infiltration", Cellular & Molecular Immunology, vol. 2, No. 6, pp. 439-448, Dec. 2005.
Forrest et al., "Immune Cell Regulation and Cardiovascular Effects of Sphingosine 1-Phosphate Receptor Agonist in Rodents Are Mediated via Distinct Receptor Subtypes", The Journal of pharmacology and experimental therapeutics (U.S Government work not protected by U.S. copyright), vol. 309, pp. 758-768, 2004.
Suzuki et al., "An immunosuppressive regimen using FTY720 combined with cyclosporin in canine kidney transplantation", Transpl Int., vol. 11, No. 2, pp. 95-101, 1998
Webb et al., "Sphingosine 1-phosphate receptor agonists attenuate relapsing-remitting experimental autoimmune encephalitis in SJL mice", J. Neuroimmun., vol. 153, No. 1, pp. 108-121 (2004).
Brinkmann V. "œ The immune modulator FTY720 . . . €• Journal of Biol. Chemistry, Americ. Society of Biolochem. Biol. vol. 277, No. 24. pp. 21453-21457.
Miller et al., Neurol. & Neurosci. Reports, (Sep. 2010), 10(5), pp. 397-406.
Hla, T., FASEB Journal, (Mar. 6, 2006), 20(4), Part 1, A20.
Maschkowskij M.D. Pharmaceuticals, Moscow, Nowaja Wolna, 2001, in 2 volumes, vol. 1 p. 11.
LaMontagne K. "ž Antagonism of Sphingosine-1-Phosphate Receptors by FTY720 Inhibits Angiogenesis . . . "œ Cancer Research, Jan. 2006, 66, 221-231. Found on: URL:http://cancerres.aacrjournals.org/content/66/1/221.ful.
Hla. T. Physiological and pathological actions of sphingosine 1-phosphate"€ Seminars in Cell & Developmental Biology, Oct. 2004, 15(5), 513-520.
Kappos L et al. "ž FTY720 in relapsing MS . . . "œ Jun. 23, 2005 online (found Jun. 2, 2011) URL:http://www.ms-in-europe.com/printversion/index.php?anr=105&cnr=4/>.

(Continued)

Primary Examiner — Kevin E Weddington
(74) Attorney, Agent, or Firm — Jim Lynch

(57) ABSTRACT

The present invention relates uses of an S1P receptor modulator such as 2-substituted 2-amino-propane-1,3-diol or 2-amino-propanol derivatives, e. g. a compound comprising a group of formula X

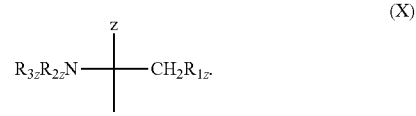

for the treatment or prevention of neo-angiogenesis associated with a demyelinating disease, e.g. multiple sclerosis.

6 Claims, No Drawings

(56) References Cited

OTHER PUBLICATIONS

Ho J.W et al. "Effects of a novel immunomodulating agent . . . " Molecular cancer theraputics, 2005 Set, 4(9), 1430-1438. Found: http://mct.aacrjournals.org/content/4/9/1430.full.pdf+html.

Virely D.J. "Developing therapeutics for the treatment of multiple sclerosis." Journal of American Society for Experimental Neuro Therapeutics. Oct. 2005, 2, 638-649. Found on: http://pubget.com/paper/16489371.

Fujino et al. 'Amelioration of experimental autoimmune encephalomyelitis . . . ' The Journal of Pharmacology and Experimental Therapeutics, vol. 305, No. 1, pp. 70-77.

K. Rammohan et al, Poster on ' Long-Term Safety of Fingolimod in Patients with Relapsing-Remitting Multiple Sclerosis: Results from Phase 3 FREEDOMS II Extension Study' Mar. 16-23, 2013, San Diego, US, 65th American Academy of Neurology Annual Meeting.

Ludwik Kappos et Al : "A place controlled trial of oral Fingolimod in relapsing multiple sclerosis", New England Journal of Medecine, Boston, MA , USA, vol. 362, No. 5, Feb. 4, 2010, pp. 387-401.

Thompson A., "FTY720 in multiple sclerosis: the emerging evidence of its therapeutic value", Core Evidence, 2006, No. 1, 3, pp. 157-167.

T.E. Schmidt et al., Multiple Sclerosis, Guide for Physicians, 2nd edition—M., MED press-inform 2010, pp. 15-16 (English Translation).

S1P RECEPTOR MODULATORS FOR TREATING RELASPING-REMITTING MULTIPLE SCLEROSIS

The present invention relates to the use of an S1P receptor modulator in the treatment or prevention of neo-angiogenesis associated with a demyelinating disease, e.g. multiple sclerosis.

S1 P receptor modulators are typically sphingosine analogues, such as 2-substituted 2-amino-propane-1,3-diol or 2-amino-propanol derivatives, e. g. a compound comprising a group of formula X.

Sphingosine-1 phosphate (hereinafter "S1P") is a natural serum lipid. Presently there are eight known S1P receptors, namely S1P1 to S1P8. S1 P receptor modulators are typically sphingosine analogues, such as 2-substituted 2-amino-propane-1,3-diol or 2-amino-propanol derivatives, e. g. a compound comprising a group of formula X

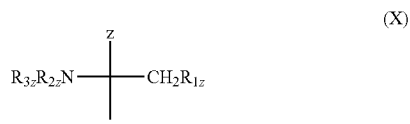

wherein Z is H, $C_{1-6}$alkyl, $C_{2-6}$alkenyl, $C_{2-6}$alkynyl, phenyl, phenyl substituted by OH, $C_{1-6}$alkyl substituted by 1 to 3 substituents selected from the group consisting of halogen, $C_{3-8}$cycloalkyl, phenyl and phenyl substituted by OH, or $CH_2$—$R_{4z}$ wherein $R_{4z}$ is OH, acyloxy or a residue of formula (a)

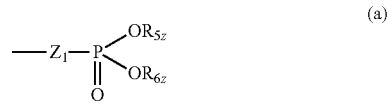

wherein $Z_1$ is a direct bond or O, preferably O;
each of $R_{5z}$, and $R_{6z}$, independently, is H, or $C_{1-4}$alkyl optionally substituted by 1, 2 or 3 halogen atoms;
$R_{1z}$ is OH, acyloxy or a residue of formula (a); and each of $R_{2z}$ and $R_{3z}$ independently, is H, $C_{1-4}$alkyl or acyl.

Group of formula X is a functional group attached as a terminal group to a moiety which may be hydrophilic or lipophilic and comprise one or more aliphatic, alicyclic, aromatic and/or heterocyclic residues, to the extent that the resulting molecule wherein at least one of Z and $R_{1z}$ is or comprises a residue of formula (a), signals as an agonist at one of more sphingosine-1-phosphate receptor.

S1P receptor modulators are compounds which signal as agonists at one or more sphingosine-1 phosphate receptors, e.g. S1P1 to S1P8. Agonist binding to a S1P receptor may e.g. result in dissociation of intracellular heterotrimeric G-proteins into Gα-GTP and Gβγ-GTP, and/or increased phosphorylation of the agonist-occupied receptor and activation of downstream signaling pathways/kinases.

The binding affinity of S1P receptor modulators to individual human S1P receptors may be determined in following assay:

S1P receptor modulator activities of compounds are tested on the human S1P receptors $S1P_1$, $S1P_2$, $S1P_3$, $S1P_4$ and $S1P_5$. Functional receptor activation is assessed by quantifying compound induced GTP [γ-$^{35}$S] binding to membrane protein prepared from transfected CHO or RH7777 cells stably expressing the appropriate human S1P receptor. The assay technology used is SPA (scintillation proximity based assay). Briefly, DMSO dissolved compounds are serially diluted and added to SPA-bead (Amersham-Pharmacia) immobilised S1P receptor expressing membrane protein (10-20 μg/well) in the presence of 50 mM Hepes, 100 mM NaCl, 10 mM $MgCl_2$, 10 μM GDP, 0.1% fat free BSA and 0.2 nM GTP [γ-$^{35}$S] (1200 Ci/mmol). After incubation in 96 well microtiterplates at RT for 120 min, unbound GTP [γ-$^{35}$S] is separated by a centrifugation step. Luminescence of SPA beads triggered by membrane bound GTP [γ-$^{35}$S] is quantified with a TOPcount plate reader (Packard). $EC_{50}$s are calculated using standard curve fitting software. In this assay, the S1P receptor modulators preferably have a binding affinity to S1P receptor <50 nM.

Preferred S1P receptor modulators are e.g. compounds which in addition to their S1P binding properties also have accelerating lymphocyte homing properties, e.g. compounds which elicit a lymphopenia resulting from a re-distribution, preferably reversible, of lymphocytes from circulation to secondary lymphatic tissue, without evoking a generalized immunosuppression. Nave cells are sequestered; CD4 and CD8 T-cells and B-cells from the blood are stimulated to migrate into lymph nodes (LN) and Peyer's patches (PP).

The lymphocyte homing property may be measured in following Blood Lymphocyte Depletion assay:

A S1P receptor modulator or the vehicle is administered orally by gavage to rats. Tail blood for hematological monitoring is obtained on day −1 to give the baseline individual values, and at 2, 6, 24, 48 and 72 hours after application. In this assay, the S1P receptor agonist or modulator depletes peripheral blood lymphocytes, e.g. by 50%, when administered at a dose of e.g. <20 mg/kg.

Examples of appropriate S1P receptor modulators are, for example:

Compounds as disclosed in EP627406A1, e.g. a compound of formula I

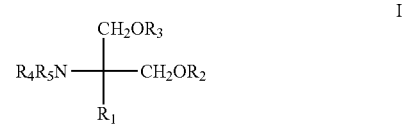

wherein $R_1$ is a straight- or branched ($C_{12-22}$) chain
which may have in the chain a bond or a hetero atom selected from a double bond, a triple bond, O, S, $NR_6$, wherein $R_6$ is H, $C_{1-4}$alkyl, aryl-$C_{1-4}$alkyl, acyl or ($C_{1-4}$alkoxy)carbonyl, and carbonyl, and/or
which may have as a substituent $C_{1-4}$alkoxy, $C_{2-4}$alkenyloxy, $C_{2-4}$alkynyloxy, aryl$C_{1-4}$alkyl-oxy, acyl, $C_{1-4}$alkylamino, acylamino, ($C_{1-4}$alkoxy)carbonyl, ($C_{1-4}$alkoxy)-carbonylamino, acyloxy, ($C_{1-4}$alkyl) carbamoyl, nitro, halogen, amino, hydroxyimino, hydroxy or carboxy; or
$R_1$ is
a phenylalkyl wherein alkyl is a straight- or branched ($C_{6-20}$)carbon chain; or
a phenylalkyl wherein alkyl is a straight- or branched ($C_{1-30}$)carbon chain wherein said phenylalkyl is substituted by
a straight- or branched ($C_{6-20}$)carbon chain optionally substituted by halogen,
a straight- or branched ($C_{6-20}$)alkoxy chain optionally substitued by halogen, a straight- or branched (C$_{6-20}$)alkenyloxy,
phenyl-C$_{1-14}$alkoxy, halophenyl-C$_{1-4}$alkoxy, phenyl-C$_{1-14}$ alkoxy-C$_{1-14}$alkyl, phenoxy-C$_{1-4}$alkoxy or phenoxy-C$_{1-4}$ alkyl,
cycloalkylalkyl substituted by C$_{6-20}$alkyl,
heteroarylalkyl substituted by C$_{6-20}$alkyl,
heterocyclic C$_{6-20}$alkyl or
heterocyclic alkyl substituted by C$_{2-20}$alkyl,
and wherein
the alkyl moiety may have
in the carbon chain, a bond or a heteroatom selected from a double bond, a triple bond, O, S, sulfinyl, sulfonyl, or NR$_6$, wherein R$_6$ is as defined above, and
as a substituent C$_{1-4}$alkoxy, C$_{2-4}$alkenyloxy, C$_{2-4}$alkynyloxy, arylC$_{1-4}$alkyloxy, acyl, C$_{1-4}$alkylamino, C$_{1-4}$alkylthio, acylamino, (C$_{1-4}$alkoxy)carbonyl, (C$_{1-4}$alkoxy)carbonylamino, acyloxy, (C$_{1-4}$alkyl)carbamoyl, nitro, halogen, amino, hydroxy or carboxy, and each of R$_2$, R$_3$, R$_4$ and R$_5$, independently, is H, C$_{1-4}$ alkyl or acyl or a pharmaceutically acceptable salt or hydrate thereof;
Compounds as disclosed in EP 1002792A1, e.g. a compound of formula II

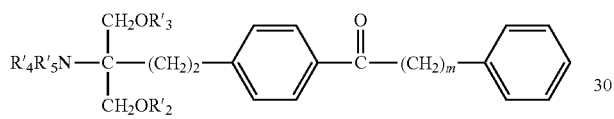

II wherein m is 1 to 9 and each of R'$_2$, R'$_3$, R'$_4$ and R'$_5$, independently, is H, C$_{1-6}$alkyl or acyl,
or a pharmaceutically acceptable salt or hydrate thereof;
Compounds as disclosed in EP0778263 A1, e.g. a compound of formula III

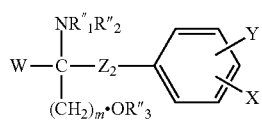

III wherein W is H; C$_{1-6}$alkyl, C$_{2-6}$alkenyl or C$_{2-6}$alkynyl; unsubstituted or by OH substituted phenyl; R"$_4$O(CH$_2$)$_n$; or C$_{1-6}$alkyl substituted by 1 to 3 substituents selected from the group consisting of halogen, C$_{3-8}$cycloalkyl, phenyl and phenyl substituted by OH;
X is H or unsubstituted or substituted straight chain alkyl having a number p of carbon atoms or unsubstituted or substituted straight chain alkoxy having a number (p-1) of carbon atoms, e.g. substituted by 1 to 3 substitutents selected from the group consisting of C$_{1-6}$alkyl, OH, C$_{1-6}$alkoxy, acyloxy, amino, C$_{1-6}$alkylamino, acylamino, oxo, haloC$_{1-6}$alkyl, halogen, unsubstituted phenyl and phenyl substituted by 1 to 3 substituents selected from the group consisting of C$_{1-6}$alkyl, OH, C$_{1-6}$alkoxy, acyl, acyloxy, amino, C$_{1-6}$alkylamino, acylamino, haloC$_{1-6}$alkyl and halogen; Y is H, OH, C$_{1-6}$alkoxy, acyl, acyloxy, amino, C$_{1-6}$alkylamino, acylamino, haloC$_{1-6}$alkyl or halogen, Z$_2$ is a single bond or a straight chain alkylene having a number or carbon atoms of q,
each of p and q, independently, is an integer of 1 to 20, with the proviso of 6≤p+q≤23, m' is 1, 2 or 3, n is 2 or 3, each of R"$_1$, R"$_2$, R"$_3$ and R"$_4$, independently, is H, C$_{1-4}$alkyl or acyl, or a pharmaceutically acceptable salt or hydrate thereof,
Compounds as disclosed in WO02/18395, e.g. a compound of formula IVa or IVb

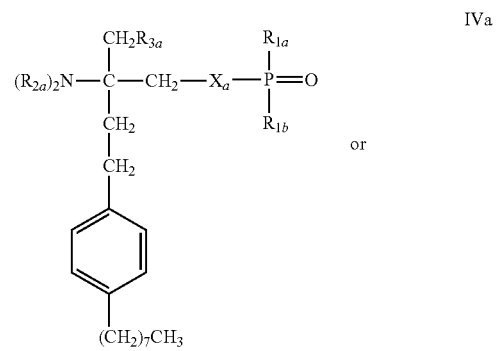

IVa or

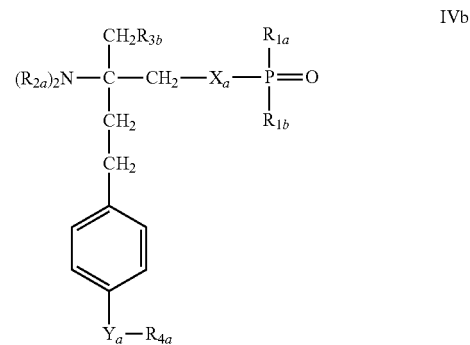

IVb wherein X$_a$ is O, S, NR$_{1a}$ or a group —(CH$_2$)$_{na}$—, which group is unsubstituted or substituted by 1 to 4 halogen; n$_a$ is 1 or 2, R$_{1a}$ is H or (C$_{1-4}$)alkyl, which alkyl is unsubstituted or substituted by halogen; R$_{1a}$ is H, OH, (C$_{1-4}$)alkyl or O(C$_{1-4}$)alkyl wherein alkyl is unsubstituted or substituted by 1 to 3 halogen; R$_{1b}$ is H, OH or (C$_{1-4}$)alkyl, wherein alkyl is unsubstituted or substituted by halogen; each R$_{2a}$ is independently selected from H or (C$_{1-4}$)alkyl, which alkyl is unsubstituted or substituted by halogen; R$_{3a}$ is H, OH, halogen or O(C$_{1-4}$)alkyl wherein alkyl is unsubstituted or substituted by halogen; and R$_{3b}$ is H, OH, halogen, (C$_{1-4}$)alkyl wherein alkyl is unsubstituted or substituted by hydroxy, or O(C$_{1-4}$)alkyl wherein alkyl is unsubstituted or substituted by halogen; Y$_a$ is —CH$_2$—, —C(O)—, —CH(OH)—, —C(=NOH)—, O or S, and R$_{4a}$ is (C$_{4-14}$)alkyl or (C$_{4-14}$)alkenyl;

or a pharmaceutically acceptable salt or hydrate thereof;
Compounds as disclosed in WO02/06268AI, e.g. a compound of formula V

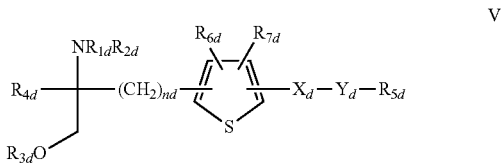

V wherein each of R$_{1d}$ and R$_{2d}$, independently, is H or an amino-protecting group;

$R_{3d}$ is hydrogen, a hydroxy-protecting group or a residue of formula

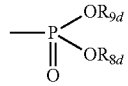

$R_{4d}$ is $C_{1-4}$alkyl;

$n_d$ is an integer of 1 to 6;

$X_d$ is ethylene, vinylene, ethynylene, a group having a formula -D-CH$_2$— (wherein D is carbonyl, —CH(OH)—, O, S or N), aryl or aryl substituted by up to three substituents selected from group a as defined hereinafter;

$Y_d$ is single bond, $C_{1-10}$alkylene, $C_{1-10}$alkylene which is substituted by up to three substitutents selected from groups a and b, $C_{1-10}$alkylene having O or S in the middle or end of the carbon chain, or $C_{1-10}$alkylene having O or S in the middle or end of the carbon chain which is substituted by up to three substituents selected from groups a and b;

$R_{5d}$ is hydrogen, $C_{3-6}$cycloalkyl, aryl, heterocyclic group, $C_{3-6}$cycloalkyl substituted by up to three substituents selected from groups a and b, aryl substituted by up to three substituents selected from groups a and b, or heterocyclic group substituted by up to three substituents selected from groups a and b;

each of $R_{6d}$ and $R_{7d}$, independently, is H or a substituent selected from group a;

each of $R_{8d}$ and $R_{9d}$, independently, is H or $C_{1-4}$alkyl optionally substituted by halogen;

<group a> is halogen, lower alkyl, halogeno lower alkyl, lower alkoxy, lower alkylthio, carboxyl, lower alkoxycarbonyl, hydroxy, lower aliphatic acyl, amino, mono-lower alkylamino, di-$C_{1-4}$alkylamino, acylamino, cyano or nitro; and <group b> is $C_{3-6}$cycloalkyl, aryl or heterocyclic group, each being optionally substituted by up to three substituents selected from group a;

with the proviso that when $R_{5d}$ is hydrogen, $Y_d$ is a either a single bond or linear $C_{1-10}$ alkylene, or a pharmacologically acceptable salt, ester or hydrate thereof;

Compounds as disclosed in JP-14316985 (JP2002316985), e.g. a compound of formula VI

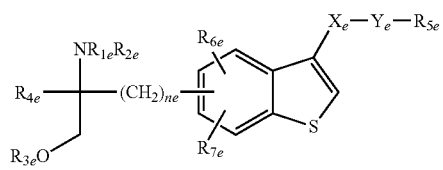

wherein $R_{1e}$, $R_{2e}$, $R_{3e}$, $R_{4e}$, $R_{5e}$, $R_{6e}$, $R_{7e}$, $n_e$, $X_e$ and $Y_e$ are as disclosed in JP-14316985;

or a pharmacologically acceptable salt, ester or hydrate thereof;

Compounds as disclosed in WO03/062252A1, e.g. a compound of formula VII

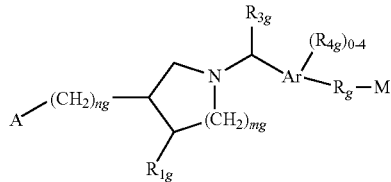

wherein

Ar is phenyl or naphthyl; each of $m_g$ and $n_g$ independently is 0 or 1; A is selected from COOH, PO$_3$H$_2$, PO$_2$H, SO$_3$H, PO($C_{1-3}$alkyl)OH and 1H-tetrazol-5-yl; each of $R_{1g}$ and $R_{2g}$ independently is H, halogen, OH, COOH or $C_{1-4}$alkyl optionally substituted by halogen; $R_{3g}$ is H or $C_{1-4}$alkyl optionally substituted by halogen or OH; each $R_{4g}$ independently is halogen, or optionally halogen substituted $C_{1-4}$alkyl or $C_{1-3}$alkoxy; and each of $R_g$ and M has one of the significances as indicated for B and C, respectively, in WO03/062252A1;

or a pharmacologically acceptable salt, solvate or hydrate thereof;

Compounds as disclosed in WO 03/062248A2, e.g. a compound of formula VIII

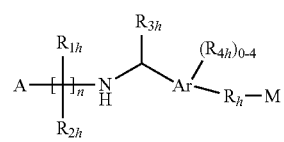

wherein Ar is phenyl or naphthyl; n is 2, 3 or 4; A is COOH, 1H-tetrazol-5-yl, PO$_3$H$_2$, PO$_2$H$_2$, —SO$_3$H or PO(R$_{5h}$)OH wherein R$_{5h}$ is selected from $C_{1-4}$alkyl, hydroxy$C_{1-4}$alkyl, phenyl, —CO—$C_{1-3}$alkoxy and —CH(OH)-phenyl wherein said phenyl or phenyl moiety is optionally substituted; each of $R_{1h}$ and $R_{2h}$ independently is H, halogen, OH, COOH, or optionally halogeno substituted $C_{1-6}$alkyl or phenyl; $R_{3h}$ is H or $C_{1-4}$alkyl optionally substituted by halogen and/OH; each $R_{4h}$ independently is halogeno, OH, COOH, S(O)$_{0, 1 \text{ or } 2}$$C_{1-3}$alkyl, $C_{1-3}$alkoxy, $C_{3-6}$cycloalkoxy, aryl or aralkoxy, wherein the alkyl portions may optionally be substituted by 1-3 halogens; and each of $R_h$ and M has one of the significances as indicated for B and C, respectively, in WO03/062248A2 or a pharmacologically acceptable salt, solvate or hydrate thereof.

Compounds as disclosed in WO 04/103306A, WO 05/000833, WO 05/103309 or WO 05/113330, e.g. compounds of formula IXa or IXb

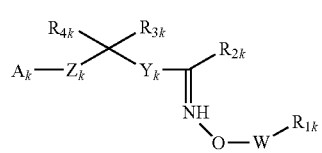

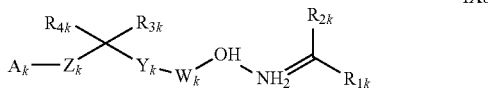

wherein $A_k$ is $COOR_{5k}$, $OPO(OR_{5k})_2$, $PO(OR_{5k})_2$, $SO_2OR_{5k}$, $POR_{5k}OR_{5k}$ or 1H-tetrazol-5-yl, $R_{5k}$ being H or $C_{1-6}$alkyl;

$W_k$ is a bond, $C_{1-3}$alkylene or $C_{2-3}$alkenylene;

$Y_k$ is $C_{6-10}$aryl or $C_{3-9}$heteroaryl, optionally substituted by 1 to 3 radicals selected from halogen, OH, $NO_2$, $C_{1-6}$alkoxy; halo-substituted $C_{1-6}$alkyl and halo-substituted $C_{1-6}$alkoxy;

$Z_k$ is a heterocyclic group as indicated in WO 04/103306A, e.g. azetidine;

$R_{1k}$ is $C_{6-10}$aryl or $C_{3-9}$heteroaryl, optionally substituted by $C_{1-6}$alkyl, $C_{6-10}$aryl, $C_{6-10}$aryl$C_{1-4}$alkyl, $C_{3-9}$heteroaryl, $C_{3-9}$heteroaryl$C_{1-4}$alkyl, $C_{3-8}$cycloalkyl, $C_{3-8}$cycloalkyl$C_{1-4}$alkyl, $C_{3-8}$heterocycloalkyl or $C_{3-8}$heterocycloalkyl$C_{1-4}$alkyl; wherein any aryl, heteroaryl, cycloalkyl or heterocycloalkyl of $R_{1k}$ may be substituted by 1 to 5 groups selected from halogen, $C_{1-6}$alkyl, $C_{1-6}$alkoxy and halo substituted-$C_{1-6}$alkyl or -$C_{1-6}$alkoxy;

$R_{2k}$ is H, $C_{1-6}$alkyl, halo substituted $C_{1-6}$alkyl, $C_{2-6}$alkenyl or $C_{2-6}$alkynyl; and each of $R_{3k}$ or $R_{4k}$, independently, is H, halogen, OH, $C_{1-6}$alkyl, $C_{1-6}$alkoxy or halo substituted $C_{1-6}$alkyl or $C_{1-6}$alkoxy;

and the N-oxide derivatives thereof or prodrugs thereof, or a pharmacologically acceptable salt, solvate or hydrate thereof.

The compounds of formulae I to IXb may exist in free or salt form. Examples of pharmaceutically acceptable salts of the compounds of the formulae I to VI include salts with inorganic acids, such as hydrochloride, hydrobromide and sulfate, salts with organic acids, such as acetate, fumarate, maleate, benzoate, citrate, malate, methanesulfonate and benzenesulfonate salts, or, when appropriate, salts with metals such as sodium, potassium, calcium and aluminium, salts with amines, such as triethylamine and salts with dibasic amino acids, such as lysine. The compounds and salts of the combination of the present invention encompass hydrate and solvate forms.

Acyl as indicated above may be a residue $R_y$—CO— wherein $R_y$ is $C_{1-6}$alkyl, $C_{3-6}$cycloalkyl, phenyl or phenyl-$C_{1-4}$ alkyl. Unless otherwise stated, alkyl, alkoxy, alkenyl or alkynyl may be straight or branched.

Aryl may be phenyl or naphthyl, preferably phenyl.

When in the compounds of formula I the carbon chain as $R_1$ is substituted, it is preferably substituted by halogen, nitro, amino, hydroxy or carboxy. When the carbon chain is interrupted by an optionally substituted phenylene, the carbon chain is preferably unsubstituted. When the phenylene moiety is substituted, it is preferably substituted by halogen, nitro, amino, methoxy, hydroxy or carboxy.

Preferred compounds of formula I are those wherein $R_1$ is $C_{13-20}$alkyl, optionally substituted by nitro, halogen, amino, hydroxy or carboxy, and, more preferably those wherein $R_1$ is phenylalkyl substituted by $C_{6-14}$-alkyl chain optionally substituted by halogen and the alkyl moiety is a $C_{1-6}$alkyl optionally substituted by hydroxy. More preferably, $R_1$ is phenyl-$C_{1-6}$alkyl substituted on the phenyl by a straight or branched, preferably straight, $C_{6-14}$alkyl chain. The $C_{6-14}$alkyl chain may be in ortho, meta or para, preferably in para.

Preferably each of $R_2$ to $R_5$ is H.

In the above formula of V "heterocyclic group" represents a 5- to 7 membered heterocyclic group having 1 to 3 heteroatoms selected from S, O and N. Examples of such heterocyclic groups include the heteroaryl groups indicated above, and heterocyclic compounds corresponding to partially or completely hydrogenated heteroaryl groups, e.g. furyl, thienyl, pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyranyl, pyridyl, pyridazinyl, pyrimidinyl, pyrazinyl, tetrahydropyranyl, morpholinyl, thiomorpholinyl, pyrrolidinyl, pyrrolyl, imidazolidinyl, pyrazolidinyl, piperidinyl, piperazinyl, oxazolidinyl, isoxazolidinyl, thiazolidinyl or pyrazolidinyl. Preferred heterocyclic groups are 5- or 6-membered heteroaryl groups and the most preferred heterocyclic group is a morpholinyl, thiomorpholinyl or piperidinyl group.

A preferred compound of formula I is 2-amino-2-tetradecyl-1,3-propanediol. A particularly preferred S1P receptor agonist of formula I is FTY720, i.e. 2-amino-2-[2-(4-octylphenyl)ethyl]propane-1,3-diol in free form or in a pharmaceutically acceptable salt form (referred to hereinafter as Compound A), e.g. the hydrochloride salt, as shown:

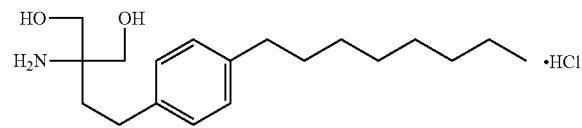 [SMILES: CCCCCCCCc1ccc(CCC(N)(CO)CO)cc1 ; Cl]

A preferred compound of formula II is the one wherein each of $R'_2$ to $R'_5$ is H and m is 4, i.e. 2-amino-2-{2-[4-(1-oxo-5-phenylpentyl)phenyl]ethyl}propane-1,3-diol, in free form or in pharmaceutically acceptable salt form (referred to hereinafter as Compound B), e.g. the hydrochloride.

A preferred compound of formula III is the one wherein W is $CH_3$, each of $R''_1$ to $R''_3$ is H, $Z_2$ is ethylene, X is heptyloxy and Y is H, i.e. 2-amino-4-(4-heptyloxyphenyl)-2-methylbutanol, in free form or in pharmaceutically acceptable salt form (referred to hereinafter as Compound C), e.g. the hydrochloride. The R-enantiomer is particularly preferred.

Compounds may be in phosphorylated form. A preferred compound of formula IVa is the FTY720-phosphate ($R_{2a}$ is H, $R_{3a}$ is OH, $X_a$ is O, $R_{1a}$ and $R_{1b}$ are OH). A preferred compound of formula IVb is the Compound C-phosphate ($R_{2a}$ is H, $R_{3b}$ is OH, $X_a$ is O, $R_{1a}$ and $R_{1b}$ are OH, $Y_a$ is O and $R_{4a}$ is heptyl). A preferred compound of formula V is Compound B-phosphate.

A preferred compound of formula VI is (2R)-2-amino-4-[3-(4-cyclohexyloxybutyl)-benzo[b]thien-6-yl]-2-methylbutan-1-ol.

A preferred compound of formula IXa is e.g. 1-{4-[1-(4-cyclohexyl-3-trifluoromethyl-benzyloxyimino)-ethyl]-2-ethyl-benzyl}-azetidine-3-carboxylic acid, or a prodrug thereof.

S1P receptor agonists or modulators are known as having immunosuppressive properties or anti-angiogenic properties in the treatment of tumors, e.g. as disclosed in EP627406A1, WO 04/103306, WO 05/000833, WO 05/103309, WO 05/113330 or WO 03/097028.

Multiple sclerosis (MS) is an immune-mediated disease of the central nervous system with chronic inflammatory demyelination leading to progressive decline of motor and sensory functions and permanent disability. The therapy of multiple sclerosis is only partially effective, and in most cases only offers a short delay in disease progression despite anti-inflammatory and immunosuppressive treatment. Accordingly, there is a need for agents which are effective in the inhibition or treatment of demyelinating diseases, e.g. multiple sclerosis or Guillain-Barré syndrome, including reduction of, alleviation of, stabilization of or relief from the symptoms which affect the organism.

Characteristic pathological features of demyelinating diseases include inflammation, demyelination and axonal and oligodendrocyte loss. In addition lesions can also have a significant vascular component. A firm link has recently been established between chronic inflammation and angiogenesis and neovascularization seems to have a significant role in the progression of disease.

It has now been found that S1P receptor modulators have an inhibitory effect on neo-angiogenesis associated with demyelinating diseases, e.g. MS.

In a series of further specific or alternative embodiments, the present invention provides:

1.1. A method for preventing, inhibiting or treating neo-angiogenesis associated with a demyelinating disease, e.g. MS, in a subject in need thereof, comprising administering to said subject a therapeutically effective amount of an S1P receptor modulator, e.g. a compound of formulae I to IXb.

1.2. A method for alleviating or delaying progression of the symptoms of a demyelinating disease, e.g. multiple sclerosis or Guillain-Barré syndrome, in a subject in need thereof, in which method neo-angiogenesis associated with said disease is prevented or inhibited, comprising administering to said subject a therapeutically effective amount of an S1P receptor modulator, e.g. a compound of formulae I to IXb.

1.3. A method for reducing or preventing or alleviating relapses in a demyelinating disease, e.g. multiple sclerosis or Guillain-Barré syndrome, in a subject in need thereof, in which method neo-angiogenesis associated with said disease is prevented or inhibited, comprising administering to said subject a therapeutically effective amount of an S1P receptor modulator, e.g. a compound of formulae I to IXb.

1.4. A method for slowing progression of a demyelinating disease, e.g. multiple sclerosis or Guillain-Barré syndrome, in a subject being in a relapsing-remitting phase of the disease, in which method neo-angiogenesis associated with said disease is prevented or inhibited, comprising administering to said subject a therapeutically effective amount of an S1P receptor modulator, e.g. a compound of formulae I to XIb.

1.5. A method as indicated above, wherein the S1P receptor modulator is administered intermittently.

For example, the S1P receptor modulator may be administered to the subject every $2^{nd}$ or $3^{rd}$ day or once a week.

2. A pharmaceutical composition for use in any one of the methods 1.1 to 1.5, comprising an S1P receptor modulator, e.g. a compound of formulae I to IXb as defined hereinabove, together with one or more pharmaceutically acceptable diluents or carriers therefor.

3. An S1P receptor modulator, e.g. a compound of formula I to IXb as defined herein above, for use in any one of the methods 1.1 to 1.5.

4. An S1P receptor modulator, e.g. a compound of formulae I to IXb as defined herein above, for use in the preparation of a medicament for use in any one of the methods 1.1 to 1.5.

Clinicians usually categorize patients having MS into four types of disease patterns:

Relapsing-remitting (RR-MS): Discrete motor, sensory, cerebellar or visual attacks that occur over 1-2 weeks and often resolve over 1-2 months. Some patients accrue disability with each episode, yet remain clinically stable between relapses. About 85% of patients initially experience the RR form of MS, but within 10 years about half will develop the secondary progressive form.

Secondary-progressive (SP-MS): Initially RR followed by gradually increasing disability, with or without relapses. Major irreversible disabilities appear most often during SP.

Primary-progressive (PP-MS): Progression disease course from onset without any relapses or remissions, affecting about 15% of MS patients.

Progressive-relapsing (PR-MS): Progressive disease from onset with clear acute relapses; periods between relapses characterized by continuing progression.

Accordingly, the S1P receptor modulators, e.g. a compound of formulae I to IXb as defined hereinabove, may be useful in the treatment of one or more of Relapsing-remitting (RR-MS), Secondary-progressive (SP-MS), Primary-progressive (PP-MS) and Progressive-relapsing (PR-MS).

In particular, the S1P receptor modulators as described herein, e.g. FTY720, i.e. 2-amino-2-[2-(4-octylphenyl)ethyl] propane-1,3-dio, are useful for treating PP-MS.

Utility of the S1P receptor modulators, e.g. the S1P receptor modulators comprising a group of formula X, in preventing or treating neo-angiogenesis associated with a demyelinating disease as hereinabove specified, may be demonstrated in animal test methods as well as in clinic, for example in accordance with the methods hereinafter described.

In Vivo: Relapsing Experimental Autoimmune Encephalomyelitis (EAE)

Disease is induced in female Lewis rats by immunization with guinea pig spinal cord tissue emulsified in complete Freund's adjuvant. This results in an acute disease within 11 days, followed by an almost complete remission around day 16 and a relapse at around days 26.

On day 26 rats are thoracectomized after having been deeply anesthetized with Isoflurane (3%, 20 L/min) and perfused through the left ventricle of the heart. The left ventricle is punctured with a 19 gauge needle from a winged infusion set (SV-19BLK; Termudo, Elkton, Md.), which is connected to an airtight pressurized syringe containing the rinsing solution (NaCl 0.9% with 250,000 U/I heparin at 35° C.). The right atrium is punctured to provide outflow, and the perfusate is infused under a precise controlled pressure of 120 mm Hg. The perfusion is continued for 5 min (at a constant rate of 20 ml/min) followed by a pre-fixation solution (2% performaldehyde in PBS at 35° C.). Finally, up to 30 ml of polyurethane resin (PUII4; Vasqtec, Zürich, Switzerland) is infused at the same rate. After 48 h, the resin-filled brain and spinal cord are excised from the animal and the soft tissue removed by maceration in 7.5% KOH during 24 hr at 50° C. The casts are then thoroughly cleaned with and stored in distilled water before drying by lyophilization. These vascular casts are quantitated using micro computer tomography.

In this assay, a S1P1 receptor modulator, e.g. Compound A significantly blocks disease-associated neo-angiogenesis when administered to the animals at a dose of from 0.1 to 20 mg/kg p.o. For example, Compound A, in the hydrochloride salt form, fully blocks disease-associated angiogenesis and completely inhibits the relapse phases when administered daily at a dose of 0.3 mg/kg p.o. The same effect is obtained when Compound A, in the hydrochloride salt form, is administered p.o. at 0.3 mg/kg every $2^{nd}$ or $3^{rd}$ day or once a week.

C. Clinical Trial

Investigation of clinical benefit of a S1P receptor agonist, e.g. a compound of formula I, e.g. Compound A.

20 patients with relapsing-remitting MS receive said compound at a daily dosage of 0.5, 1.25 or 2.5 mg p.o. The general clinical state of the patient is investigated weekly by physical and laboratory examination. Disease state and changes in disease progression are assessed every 2 months by radiological examination (MRI) and physical examination. Initially patients receive treatment for 2 to 6 months. Thereafter, they remain on treatment for as long as their disease does not progress and the drug is satisfactorily tolerated.

Main variables for evaluation: Safety (adverse events), standard serum biochemistry and hematology, magnetic resonance imaging (MRI).

Daily dosages required in practicing the method of the present invention when a S1P receptor modulator alone is used will vary depending upon, for example, the compound used, the host, the mode of administration and the severity of the condition to be treated. A preferred daily dosage range is about from 0.1 to 100 mg as a single dose or in divided doses. Suitable daily dosages for patients are on the order of from e.g. 0.1 to 50 mg p.o. The S1P receptor modulator may be administered by any conventional route, in particular enterally, e.g. orally, e.g. in the form of tablets, capsules, drink solutions, nasally, pulmonary (by inhalation) or parenterally, e.g. in the form of injectable solutions or suspensions. Suitable unit dosage forms for oral administration comprise from ca. 0.1 to 30 mg, usually 0.25 to 30 mg S1P receptor modulator, together with one or more pharmaceutically acceptable diluents or carriers therefore. As already mentioned, the S1P receptor modulator, e.g. Compound A, may alternatively be administered intermittently, e.g. at a dose of 0.5 to 30 mg every other day or once a week.

According to another embodiment of the invention, the S1P receptor modulator may be administered as the sole active ingredient or in conjunction with, e.g. as an adjuvant to, a VEGF-receptor antagonist.

Examples of suitable VEGF-receptor antagonist include e.g. compounds, proteins or antibodies which inhibit the VEGF receptor tyrosine kinase, inhibit a VEGF receptor or bind to VEGF, and are e.g. in particular those compounds, proteins or monoclonal antibodies generically and specifically disclosed in WO 98/35958, e.g. 1-(4-chloroanilino)-4-(4-pyridylmethyl)phthalazine or a pharmaceutically acceptable salt thereof, e.g. the succinate, in WO 00/27820, e.g. a N-aryl(thio) anthranilic acid amide derivative e.g. 2-[(4-pyridyl)methyl]amino-N-[3-methoxy-5-(trifluoromethyl)phenyl]benzamide or 2-[(1-oxido-4-pyridyl)methyl]amino-N-[3-trifluoromethylphenyl]benzamide, or in WO 00/09495, WO 00/59509, WO 98/11223, WO 00/27819, WO 01/55114, WO 01/58899 and EP 0 769 947; those as described by M. Prewett et al in Cancer Research 59 (1999) 5209-5218, by F. Yuan et al in Proc. Natl. Acad. Sci. USA, vol. 93, pp. 14765-14770, December 1996, by Z. Zhu et al in Cancer Res. 58, 1998, 3209-3214, and by J. Mordenti et al in Toxicologic Pathology, Vol. 27, no. 1, pp 14-21, 1999; in WO 00/37502 and WO 94/10202; Angiostatin™, described by M. S. O'Reilly et al, Cell 79, 1994, 315-328; Endostatin™, described by M. S. O'Reilly et al, Cell 88, 1997, 277-285; anthranilic acid amides; ZD4190; ZD6474; SU5416; SU6668; or anti-VEGF antibodies or anti-VEGF receptor antibodies, e.g. RhuMab.

4-Pyridylmethyl-phthalazine derivatives are e.g. preferred inhibitors of VEGF receptor tyrosine kinase. Such derivatives and their preparation, pharmaceutical formulations thereof and methods of making such compounds are described in WO00/59509, EP02/04892, WO01/10859 and, in particular, in U.S. Pat. No. 6,258,812, which are here incorporated by reference.

Where the S1P receptor modulator is administered in conjunction with a VEGF-receptor antagonist, dosages of the co-administered VEGF-receptor agonist will of course vary depending on the type of co-drug employed, e.g. whether it is a steroid or a calcineurin inhibitor, on the specific drug employed, on the condition being treated and so forth. In accordance with the foregoing the present invention provides in a yet further aspect:

5. A method as defined above comprising co-administration, e.g. concomitantly or in sequence, of a therapeutically effective non-toxic amount of a S1P receptor modulator and a VEGF-receptor antagonist, e.g. as indicated above.
6. A pharmaceutical combination, e.g. a kit, comprising a) a first agent which is a S1P receptor modulator as disclosed herein, in free form or in pharmaceutically acceptable salt form, and b) a VEGF-receptor antagonist, e.g. as indicated above. The kit may comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a S1P receptor modulator and a VEGF-receptor antagonist, are both administered to a patient simultaneously in the form of a single entity or dosage. The term "non-fixed combination" means that the active ingredients, e.g. a S1P receptor modulator and a VEGF-receptor antagonist, are both administered to a patient as separate entities either simultaneously, concurrently or sequentially with no specific time limits, wherein such administration provides therapeutically effective levels of the 2 compounds in the body of the patient.

The invention claimed is:

1. A method for reducing or preventing or alleviating relapses in Relapsing-Remitting multiple sclerosis in a subject in need thereof, comprising orally administering to said subject 2-amino-2-[2-(4-octylphenyl)ethyl]propane-1,3-diol, in free form or in a pharmaceutically acceptable salt form, at a daily dosage of 0.5 mg, absent an immediately preceding loading dose regimen.

2. The method according to claim 1 wherein 2-amino-2-[2-(4-octylphenyl)ethyl]propane-1,3-diol hydrochloride is administered.

3. A method for treating Relapsing-Remitting multiple sclerosis in a subject in need thereof, comprising orally administering to said subject 2-amino-2-[2-(4-octylphenyl)ethyl]propane-1,3-diol, in free form or in a pharmaceutically acceptable salt form, at a daily dosage of 0.5 mg, absent an immediately preceding loading dose regimen.

4. The method according to claim 3 wherein 2-amino-2-[2-(4-octylphenyl)ethyl]propane-1,3-diol hydrochloride is administered.

5. A method for slowing progression of Relapsing-Remitting multiple sclerosis in a subject in need thereof, comprising orally administering to said subject 2-amino-2-[2-(4-octylphenyl)ethyl]propane-1,3-diol, in free form or in a pharmaceutically acceptable salt form, at a daily dosage of 0.5 mg, absent an immediately preceding loading dose regimen.

6. The method according to claim 5 wherein 2-amino-2-[2-(4-octylphenyl)ethyl]propane-1,3-diol hydrochloride is administered.

\* \* \* \* \*